(12) United States Patent
Tybinkowski et al.

(10) Patent No.: US 6,955,464 B1
(45) Date of Patent: Oct. 18, 2005

(54) HORIZONTAL DRIVE APPARATUS AND METHOD FOR PATIENT TABLE

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 379 days.

(21) Appl. No.: 10/161,810

(22) Filed: Jun. 3, 2002

Related U.S. Application Data

(60) Provisional application No. 60/295,135, filed on Jun. 1, 2001.

(51) Int. Cl.$^7$ .............................. A61B 6/04; A47B 1/10
(52) U.S. Cl. ..................... 378/209; 108/143; 108/5; 108/601
(58) Field of Search .................... 5/600, 601; 378/209, 378/20, 208; 108/143; 600/415

(56) References Cited

U.S. PATENT DOCUMENTS

| | | | |
|---|---|---|---|
| 3,588,500 A * | 6/1971 | Koerner | 5/601 |
| 3,814,414 A * | 6/1974 | Chapa | 5/601 |
| 4,131,802 A | 12/1978 | Braden et al. | |
| 4,262,204 A * | 4/1981 | Mirabella | 378/20 |
| 4,567,894 A | 2/1986 | Bergman | |
| 4,568,071 A | 2/1986 | Rice | |
| 4,576,368 A | 3/1986 | Ogawa et al. | |
| 4,613,122 A | 9/1986 | Manabe | |
| 4,727,328 A | 2/1988 | Carper et al. | |
| 4,773,637 A * | 9/1988 | Jarin | 5/600 |
| 4,914,682 A | 4/1990 | Blumenthal | |
| 4,984,774 A | 1/1991 | Zupancic et al. | |
| 5,058,871 A | 10/1991 | Congin et al. | |
| 5,066,915 A | 11/1991 | Omori et al. | |
| 5,199,123 A | 4/1993 | Jacques et al. | |
| 5,204,629 A | 4/1993 | Ueyama | |
| 5,210,893 A * | 5/1993 | Uosaki et al. | 5/601 |
| 5,273,043 A | 12/1993 | Ruike | |
| 5,475,885 A | 12/1995 | Ishikawa | |
| 5,590,429 A * | 1/1997 | Boomgaarden et al. | 5/600 |
| 5,596,779 A * | 1/1997 | Meek | 5/600 |
| 5,657,498 A | 8/1997 | Hum | |
| 5,960,054 A | 9/1999 | Freeman et al. | |
| 6,499,159 B1 * | 12/2002 | Schmitt et al. | 5/601 |
| 6,615,428 B1 * | 9/2003 | Pattee | 5/601 |
| 6,637,056 B1 * | 10/2003 | Tybinkowski et al. | 5/611 |

* cited by examiner

*Primary Examiner*—Michael Safavi
(74) *Attorney, Agent, or Firm*—McDermott Will & Emery LLP

(57) ABSTRACT

A patient table including an elongated table assembly extending between opposing ends, an elongated pallet mounted on the table assembly for linear motion between the opposing ends of the table assembly, and an elongated horizontal drive apparatus including a rotary motor, and an elongated rotary-to-linear motion converting mechanism extending between the opposing ends of the table assembly and substantially positioned at a midpoint between opposing sides of the table assembly. The rotary-to-linear motion converting mechanism connects the rotary motor to the pallet such that operation of the motor causes linear motion of the pallet on the table assembly. Among other feature and advantages, the centrally located rotary-to-linear motion converting mechanism has been found to provide smooth movement of the pallet on the table assembly.

18 Claims, 11 Drawing Sheets

HORIZONTAL DRIVE APPARATUS AND METHOD FOR PATIENT TABLE

CROSS-REFERENCE TO RELATED APPLICATIONS

The present application claims priority to provisional U.S. patent application Ser. No. 60/295,135, which was filed on Jun. 1, 2001, now abandoned is assigned to the assignee of the present application, and is incorporated herein by reference.

The present application is also related to U.S. Pat. No. 6,637,056, entitled LIFTING APPARATUS AND METHOD FOR PATIENT TABLE, which is assigned to the assignee of the present application and incorporated herein by reference.

FIELD OF THE INVENTIONS

The present inventions relate generally to tomography systems and, more particularly, to a table for supporting a sample, such as a patient, in a tomography scanner during a scanning procedure. Even more particularly, the present inventions relate to a horizontal drive apparatus and method for a patient table.

BACKGROUND OF THE INVENTIONS

Medical diagnostic imaging and scanner systems such as magnetic resonance imaging (MRI) apparatus, X-ray machines, positron emission tomography (PET) scanners, and computer tomography (CT) scanners are well known. Such machines are quite popular as a tool for providing images of internal portions of patients for diagnosis of medical conditions, such as internal injuries, cancerous tumors and the like. Owing to good quality tomographic images with low dosage X-ray radiation, the CT scanner has become especially well accepted by the medical profession for examining patients and diagnosing medical conditions.

An annular gantry normally supports many of the components of a CT scanner and includes an outer ring secured to a stand and an inner ring mounted for rotation within the outer ring. During a scanning procedure, a pallet of a patient table is extended through the center of the gantry and the inner ring is rotated about the pallet. A patient lies on the pallet within the center of the gantry during the scanning procedure. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

In order to obtain tomographic images of a patient with a CT scanner or X-ray CT apparatus, it is necessary that the patient be located exactly at a predetermined position inside the opening of an annular scan gantry of the apparatus. For this reason, such apparatus has been provided with a patient handling couch or table which is moveable vertically to be in line with an axis of rotation of the scan gantry, and then moveable horizontally, or axially in and out of the scan gantry parallel with the axis of rotation.

Several patient tables are known for this purpose. For example, U.S. patents showing various patient tables include: U.S. Pat. Nos. 4,131,802; 4,567,894; 4,568,071; 4,576,368; 4,613,122; 4,727,328; 4,914,682; 4,984,774; 5,058,871; 5,066,915; 5,199,123; 5,204,629; 5,273,043; 5,657,498; and 5,960,054. Many of these patents show patient tables having horizontally extendable patient pallets.

What is still desired, however, is a new and improved patient table for use with medical diagnostic imaging and scanner systems. In particular, what is desired a patient table having an improved horizontal drive apparatus for horizontally moving a pallet of the patient table. Among other features and advantages, the new and improved horizontal drive apparatus will preferably be a simple, yet reliable and robust design, and will relatively smoothly extend and retract the pallet such that a patient lying on the pallet can be correctly positioned in a scanning machine in a comfortable manner.

A patient table including the horizontal drive apparatus of the present invention will preferably also be provided with new and improved structural members. Among other features and advantages, the new and improved structural members will greatly simplify the design, the assembly and the overall cost of the patient table.

In addition, a patient table including the horizontal drive apparatus of the present invention will preferably be provided with a new and improved sensor assembly for providing an indication of the horizontal position of the pallet during operation of the horizontal drive apparatus. Among other features and advantages, the new and improved sensor assembly will provide extremely accurate and consistent horizontal position measurements.

Preferably, a patient table including the horizontal drive apparatus of the present invention will also be provided with a new and improved bearing assembly for supporting the pallet. Among other features and advantages, the new and improved bearing assembly will allow the pallet to be easily and quickly centered on the patient table.

SUMMARY OF THE INVENTIONS

The present inventions provide a new and improved patient table. A patient table constructed in accordance with the present inventions can be used for, but is not limited to, positioning a patient within an imaging gantry of a tomography scanner system.

According to one exemplary embodiment of the present inventions, the patient table includes an elongated table assembly extending between opposing ends, an elongated pallet mounted on the table assembly for linear motion between the opposing ends of the table assembly, and an elongated horizontal drive apparatus including a rotary motor, and an elongated rotary-to-linear motion converting mechanism extending between the opposing ends of the table assembly. The motion converting mechanism is substantially positioned at a midpoint between opposing sides of the table assembly and connects the rotary motor to the pallet such that operation of the motor causes linear motion of the pallet on the table assembly. Among other feature and advantages, the centrally located motion converting mechanism has been found to provide smooth movement of the pallet on the table assembly.

Among other features and advantages, the new and improved horizontal drive apparatus is a simple, yet reliable and robust design, and relatively smoothly extends and retracts the pallet such that a patient lying on the pallet can be correctly positioned in a scanning machine in a comfortable manner.

According to an additional exemplary embodiment of the present inventions, the table assembly is constructed from at least two extruded pieces. Among other features and advantages, the extruded pieces greatly simplify the design, the assembly and the overall cost of the patient table.

According to an additional exemplary embodiment of the present inventions, the patient table includes a sensor assembly having a magnet secured to one of the pallet and the table assembly, and a magnetic absolute linear position sensor secured to the other of the pallet and the table assembly. Among other features and advantages, the new and improved sensor assembly provides extremely accurate and consistent horizontal position measurements.

According to another exemplary embodiment of the present inventions, the patient table includes tracks mounted on opposing sides of the table assembly and extending between the opposing ends of the table assembly, and a carriage received on the tracks for movement along the tracks between the opposing ends of the table assembly, and wherein the pallet is secured to the carriage. A new and improved bearing assembly supporting the carriage on the tracks includes at least one cassette slidingly received on each of the tracks, supports connected to the carriage and positioned adjacent the cassettes, sleeves adjustably received within bores of the supports, and fasteners adjustably extending through the sleeves and secured in bores of the cassettes. Among other features and advantages, the new and improved bearing assembly allows the pallet to be easily and quickly centered between the tracks on the patient table.

The foregoing and other features and advantages of the present inventions will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
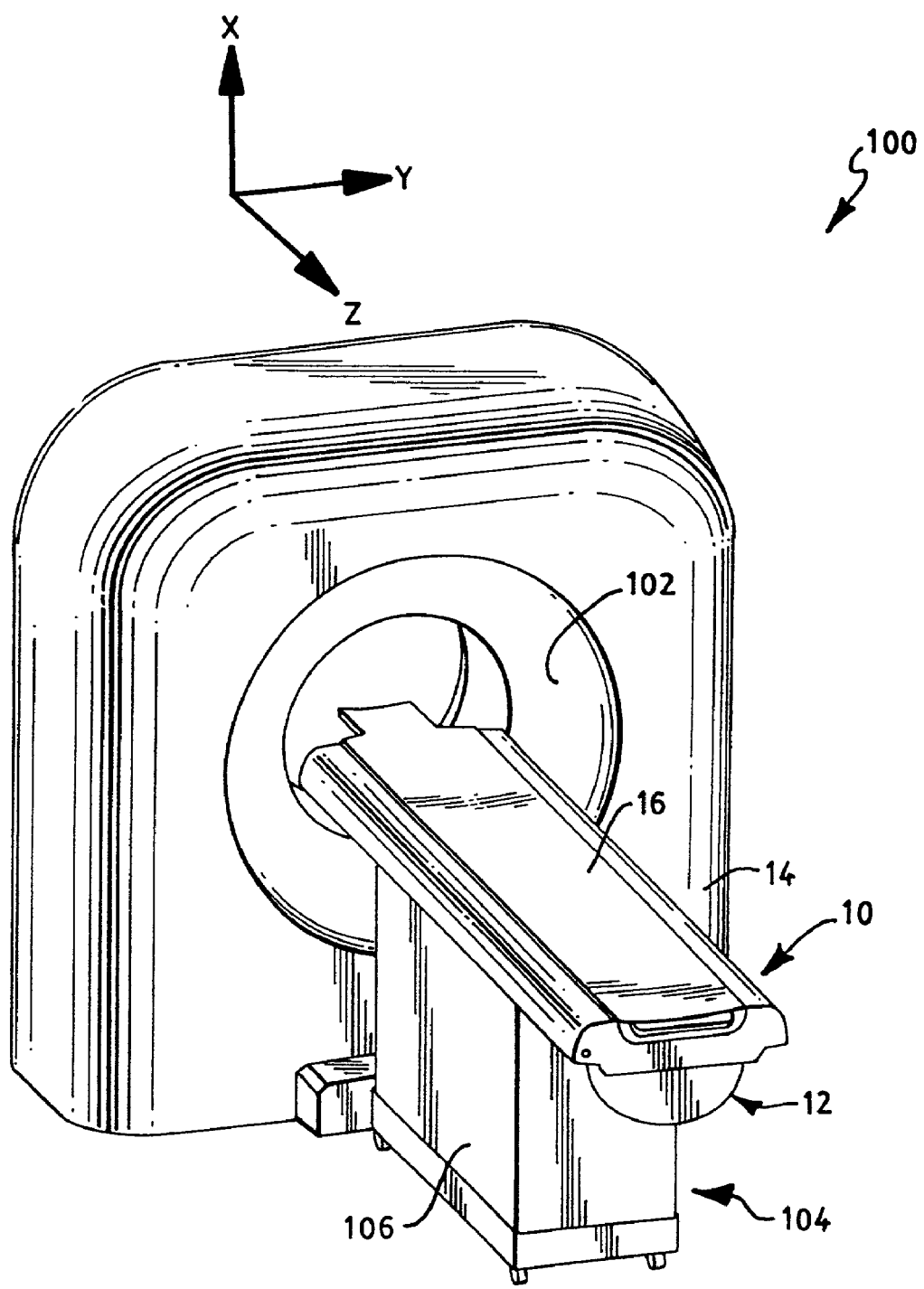
FIG. 1 is a top and end perspective view of an exemplary embodiment of a patient table constructed in accordance with the present inventions, wherein the table is shown in a fully raised position and positioned with respect to a tomography scanner system such that a patient supported on a pallet of the patient table would be generally aligned with an axis of rotation of a gantry of the tomography scanner system.

Referring first to FIG. 1, an x-ray tomography scanner system 100 is shown with an exemplary embodiment of a patient table 10 constructed in accordance with the present inventions. Among other features and advantages, the patient table 10 of the present inventions has an improved horizontal drive apparatus 12, improved structural members 18, 20, 22, an improved horizontal position sensor assembly 60, and an improved bearing assembly 70.

As is known to one skilled in the art of x-ray tomography scanning, the scanner system 100 includes an annular gantry 102 containing therein an x-ray source that projects a beam of x-rays toward a detector array on an opposite side of the gantry 102. During a scanning procedure, the annular gantry 102 and the components mounted thereon rotate about a center of rotation, which is parallel and aligned with a z-axis of a Cartesian coordinate system shown in FIG. 1. The x-ray beam is collimated to lie within in an x-y plane of the Cartesian coordinate system and pass through a patient lying on the patient table 10 within an opening of the gantry 102. The detector array within the gantry 102 senses the projected x-rays that pass through the patient and produces electrical signals that represent the intensity of the attenuation of the x-ray beam passing through the patient.

Although not shown, rotation of the gantry 102 and the operation of the x-ray source are governed by a control mechanism of the scanner system 100. The control mechanism includes an x-ray controller that provides power and timing signals to the x-ray source within the gantry and a gantry motor controller that controls the rotational speed and position of the gantry 102. A data acquisition system (DAS) of the control mechanism samples analog data from the detector array of the gantry 102 and converts the data to digital signals for subsequent processing. An image reconstructor receives the sampled and digitized x-ray data from the DAS and performs high speed image reconstruction, which is applied as an input to a computer which stores the image in a mass storage device.

The computer of the control mechanism of the scanner system 100 in turn receives commands and scanning parameters from an operator via an input device, such as a keyboard, and a video display allows the operator to observe the reconstructed image and other data from computer. The operator supplied commands and parameters are used by the computer to provide control signals and information to the DAS, the x-ray controller and the gantry motor controller.

The computer of the scanner system 100 can also be used to control operation of the patient table 10 to correctly position a patient through the central opening in the gantry 102. In particular, after the patient table 10 is correctly positioned with respect to the gantry 102, as shown in FIG. 1, the patient table 10 is operated to lift a patient vertically (parallel with the x-axis) to a desired position with respect to the rotation axis (z-axis) of the gantry before beginning a scanning procedure. During the scanning procedure, the patient table 10 is then operated to move a patient horizontally through the annular gantry 102 in a direction parallel with the rotation axis (z-axis) of the gantry.

Referring also to FIGS. 2 through 6, the patient table 10 includes an elongated table assembly 14 and an elongated pallet 16 positioned on the table assembly. As shown, the table 10 is positioned with respect to the gantry 102 such that the elongated pallet 16 extends parallel with the rotation axis (z-axis) of the gantry 102. The elongated pallet 16 is shaped and sized for a patient to lie thereon in alignment with the rotation axis (z-axis) of the gantry 102. The pallet 16 and the table assembly 14 include the new and improved horizontal drive apparatus 12 constructed in accordance with the present invention for moving the pallet 16 in a horizontal direction on the table assembly 14 parallel with the rotation axis (z-axis) of the gantry 102. In this manner, the pallet 16 can be extended through the opening of the gantry 102 with a patient thereon during a scanning procedure. Among other features and advantages, the horizontal drive apparatus 12 of the present inventions provides relatively smooth horizontal movement of the pallet 16 of the patient table 10.

In addition to the horizontal drive apparatus 12, the table 10 includes a new and improved lifting apparatus 104 supporting the table assembly 14 and the pallet 16. The lifting apparatus 104 is used to lift the table assembly 14, the pallet 16 and a patient supported thereon, vertically (parallel with the x-axis) to a desired position with respect to the rotation axis (z-axis) of the gantry 102 before beginning a scanning procedure. Among other advantages, the lifting apparatus 104 provides a combination of both vertical (parallel with the x-axis) and horizontal (parallel with the z-axis) movement of the patient table during operation. The lifting apparatus 104 also nests in its lowered position in order to minimize the table's overall height when lowered. The lifting apparatus 104 is described and claimed in detail in U.S. Pat. No. 6,637,056, entitled LIFTING APPARATUS AND METHOD FOR PATIENT TABLE, which is assigned to the assignee of the present application and incorporated herein by reference. The lifting apparatus 104 includes a cover assembly 106 which is shown removed in FIG. 4.

Figure 2:
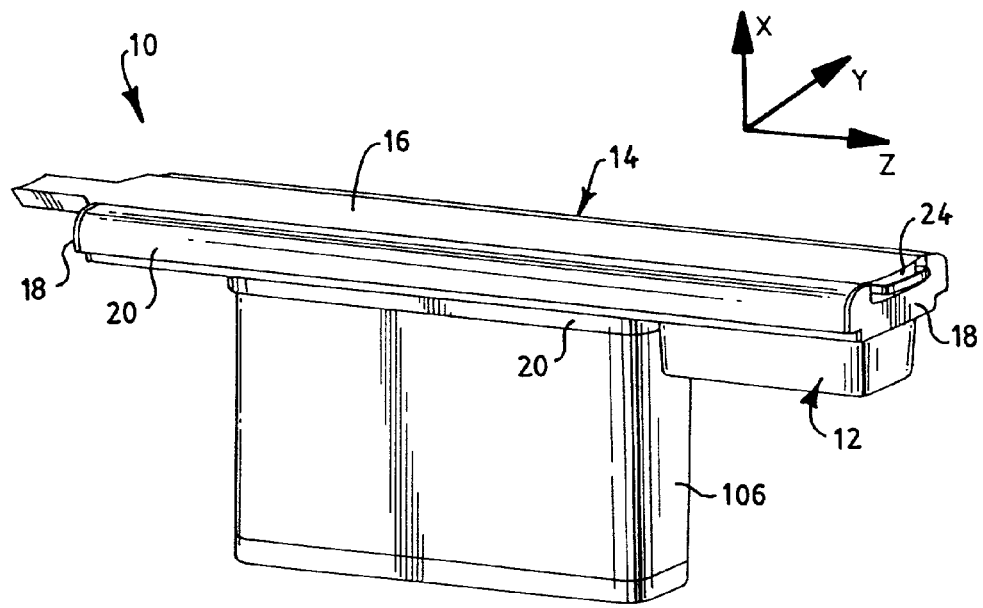
FIG. 2 is a top and end perspective view of the patient table of FIG. 1, wherein the table is shown in the fully raised position.
Figure 3:
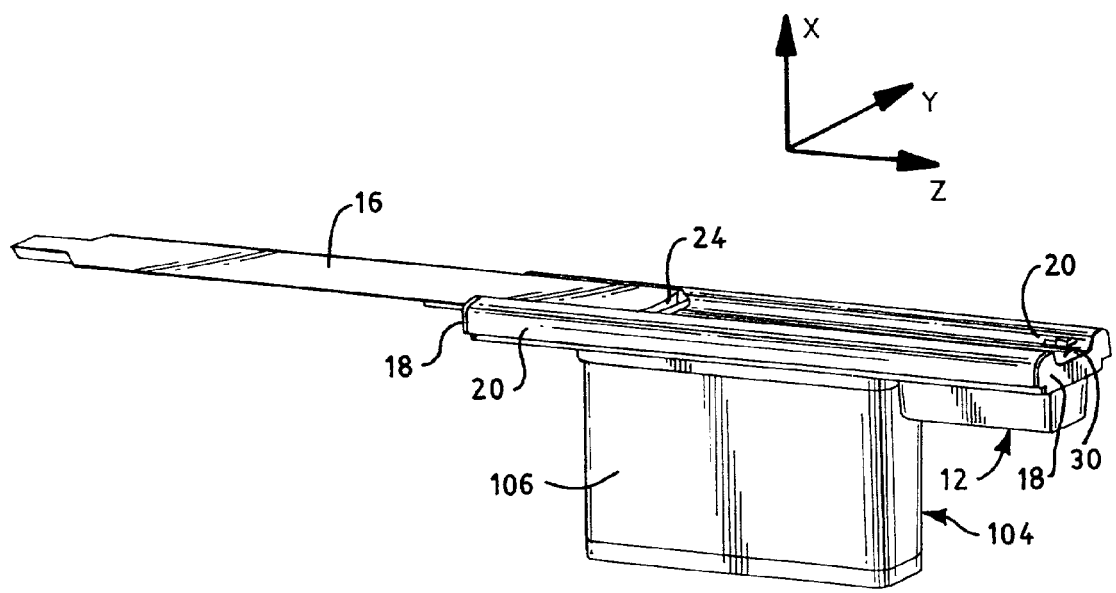
FIG. 3 is a top and end perspective view of the patient table of FIG. 1, wherein the table is shown in a fully raised position and with the pallet of the table horizontally extended.

Referring to FIGS. 1 through 3, the table assembly 14 includes new and improved structural members comprising end plates 18 and side plates 20 that are made from a relatively lightweight and inexpensive, yet rigid and strong, material, such as aluminum or a plastic. The side plates 20 are identical and preferably manufactured through an extrusion process to reduce their costs. Referring to FIGS. 4, 10, 12 and 13, the new and improved structural members of the table assembly 14 also includes two elongated rails 22 secured to an upper base 105 of the lifting apparatus 104 (with "upper" and "lower" being made with reference to the x-axis in the figures). The rails 22 are made from a relatively lightweight and inexpensive, yet rigid and strong, metal, such as aluminum. The rails 22 are identical and preferably manufactured through an extrusion process to reduce their costs. The side plates 20 are assembled to the rails 22, in a snap-fit manner for example, and the end plates 18 are secured to ends of the side plates 20 and ends of the rails 22, with screws for example. Among other features and advantages, the use of extruded side plates 20 and extruded rails 22 greatly simplifies the design, the assembly, and the overall cost of the patient table 10.

Figure 4:
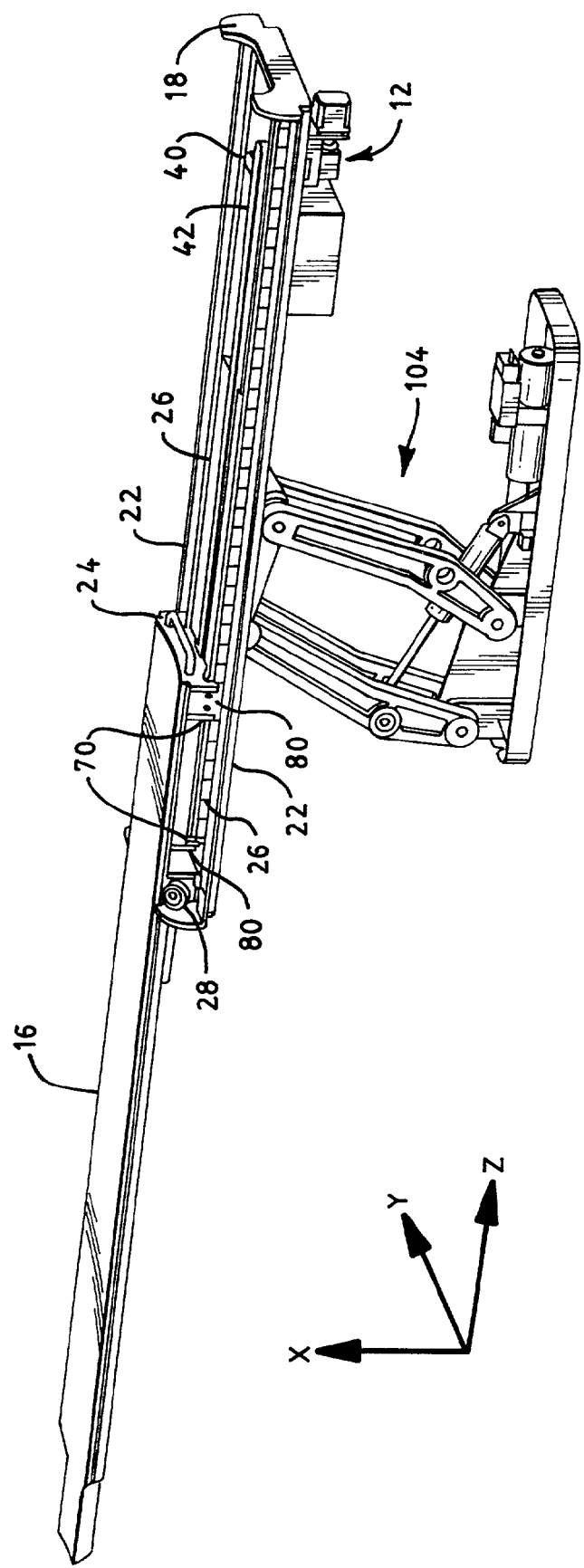
FIG. 4 is a top and end perspective view of the patient table of FIG. 1, wherein the table is shown in a fully raised position and with the pallet of the table horizontally extended, and wherein side plates and a top cover plate of a table assembly of the table are shown removed to reveal a horizontal drive apparatus and carriage for the pallet, and a cover assembly of the table is shown removed to reveal a lifting apparatus of the table.
Figure 10:
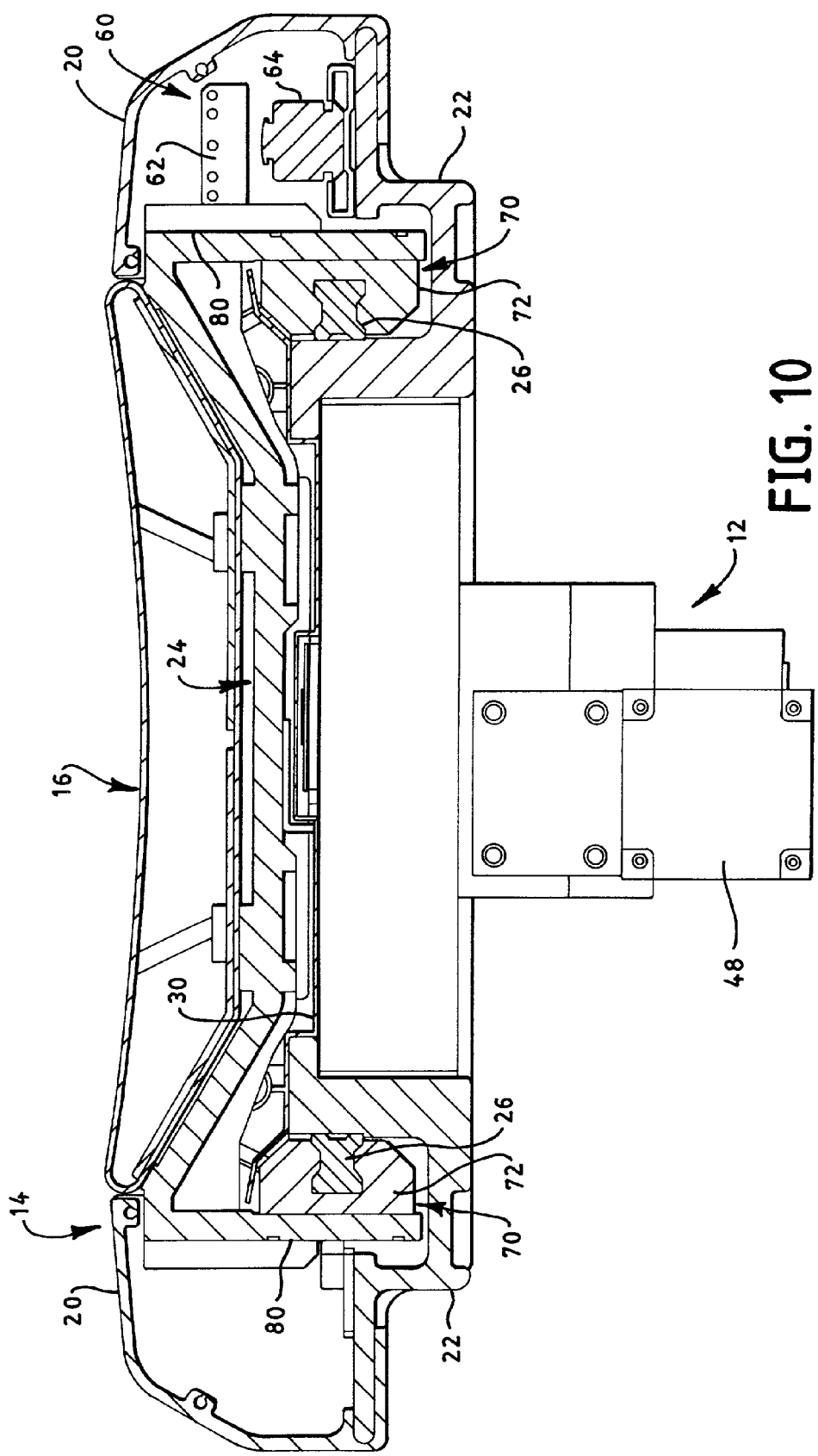
FIG. 10 is a sectional view of the patient table of FIG. 1, taken along line 10—10 of FIG. 8 and wherein the side plates of the table assembly of the table are shown attached.

As shown best in FIGS. 4 and 10, the pallet 16 is supported on a carriage 24 that is slidably mounted on tracks 26 secured to the rails 22 of the table assembly 14. As shown best in FIGS. 4 and 5, the table assembly 14 also includes rollers 28 positioned at front ends (with "front" and "rear" being made with reference to the z-axis in the figures) of the rails 22 for supporting the movable pallet 16. As shown best in FIG. 10, the table assembly 14 can also include a top cover plate 30 positioned between the rails 22 and the carriage 24 for covering the horizontal drive apparatus 12 such that the horizontal drive apparatus is not exposed when the pallet 16 is horizontally extended from the table assembly 14, as shown in FIG. 3.

Figure 5:
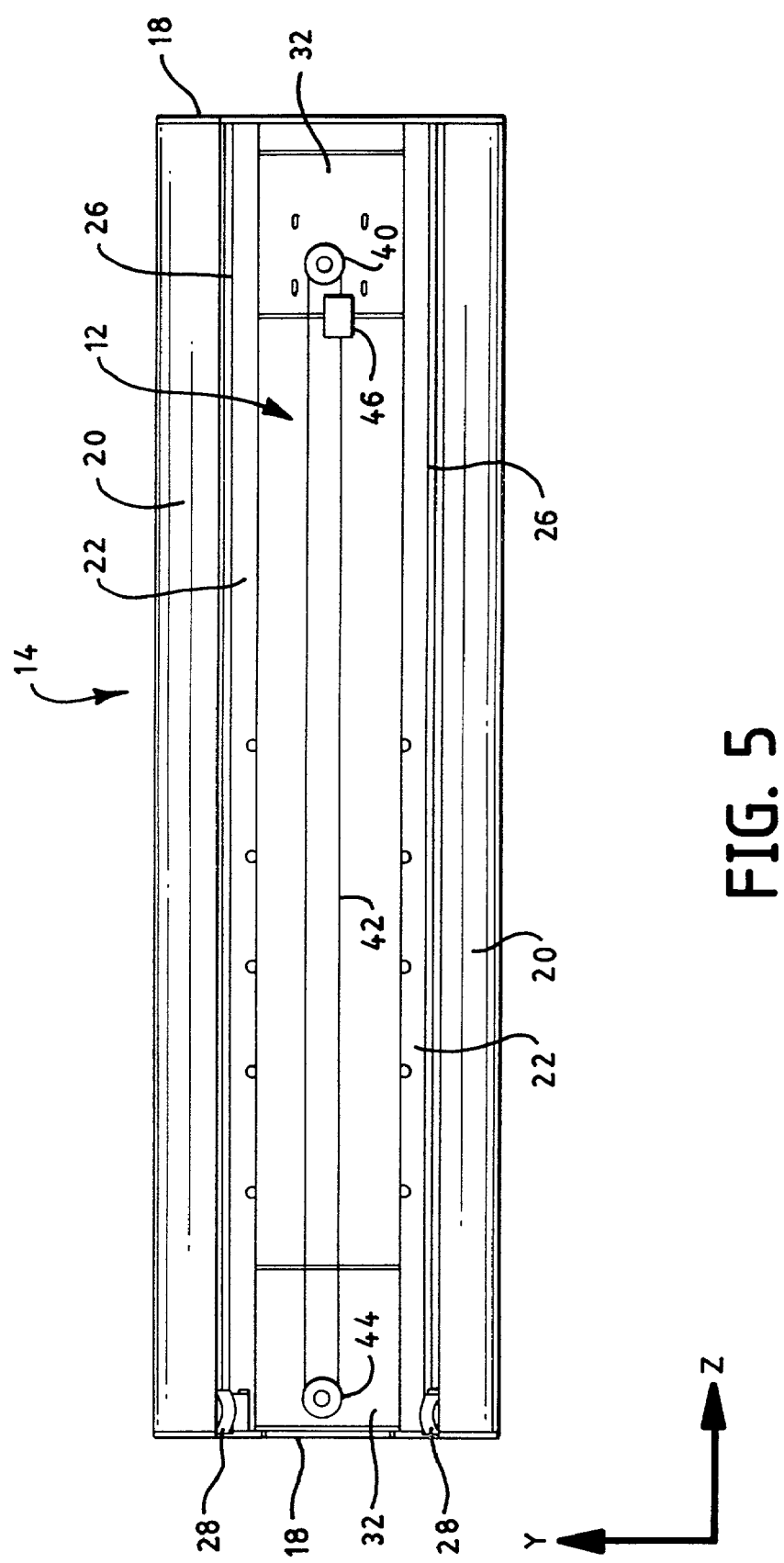
FIG. 5 is a top plan view of the patient table of FIG. 1, wherein the pallet and the carriage are removed, and the top cover plate of the table assembly is removed, to reveal the horizontal drive apparatus of the table.

Referring to FIG. 5, the horizontal drive apparatus 12 is centrally located between the rails 22 within the table assembly 14 (with "centrally located" being made with reference to the y-axis in the figures). The horizontal drive apparatus 12 generally includes a rotary motor 48 and an elongated rotary-to-linear motion converting mechanism extending between the opposing ends of the table assembly 14 and substantially positioned at a midpoint between opposing sides of the table assembly 14. The rotary-to-linear motion converting mechanism connects the rotary motor 48 to the pallet 16 such that operation of the motor 48 causes linear motion of the pallet 16 on the table assembly 14.

In one exemplary embodiment of the present invention, the rotary-to-linear motion converting mechanism comprises a timing pulley 40 rotatably mounted on a floor plate 32 of the table assembly 14 adjacent a rear end of the table assembly 14. The timing pulley 40 in turn drives a timing belt 42 extending between the timing pulley 40 and an idler pulley 44 rotatably mounted on the floor plate 32 of the table assembly 14 and positioned adjacent a front end of the table assembly 14. The carriage 24 which supports the pallet 16 is secured to the timing belt 42 through a clamp 46 such that rotation of the timing pulley 40 causes linear movement of the clamp 46 and the carriage 24.

Figure 6:
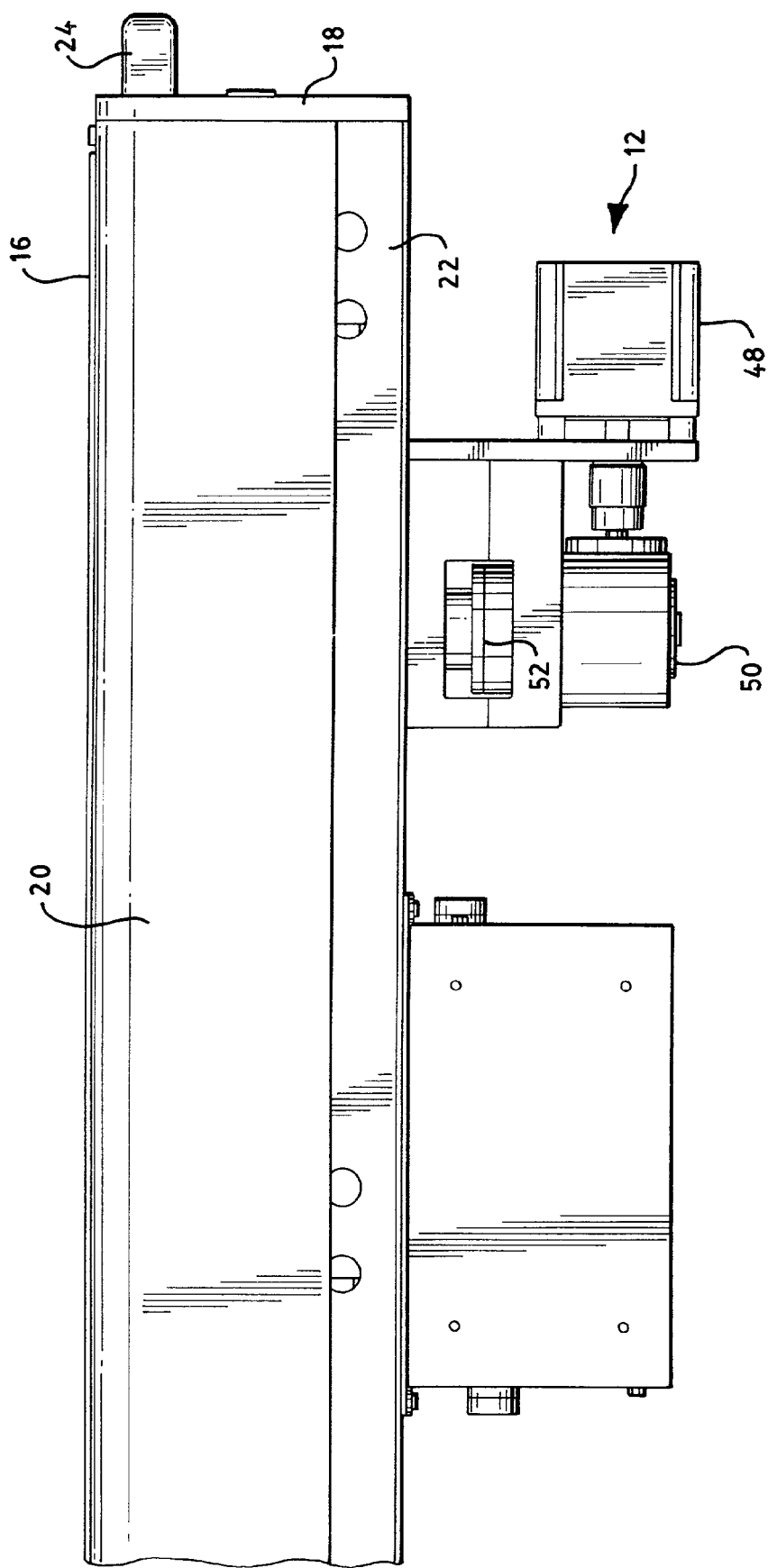
FIG. 6 is an enlarged side elevation view of a portion of the patient table of FIG. 1, showing a motor, gear reducer, and clutch mechanism for the horizontal drive apparatus of the table.
Figure 7:
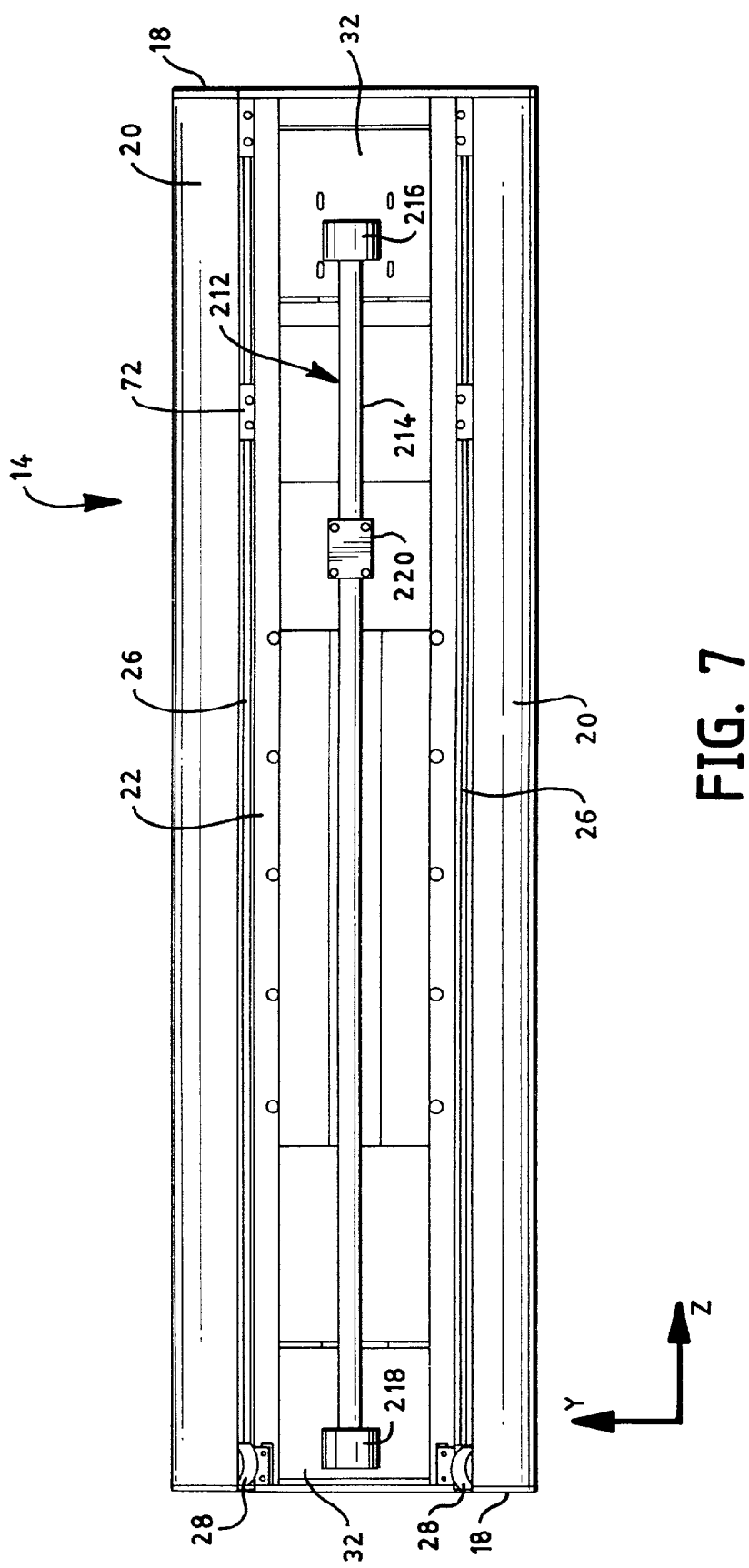
FIG. 7 is a top plan view of a patient table similar to the patient table of FIG. 1, wherein the pallet and the carriage are removed, and the top cover plate of the table assembly is removed, to reveal another horizontal drive apparatus constructed in accordance with the present inventions.

Referring to FIG. 6, the rotary motor 48 is connected through the floor plate 32 of the table assembly 14 to the timing pulley 40 through a gear reducer 50 and a clutch 52. The clutch is preferably a free floating clutch 52, which provides smoother engagement and eliminates 'chatter'. Operation of the motor 48 causes rotation of the timing pulley 40 and horizontal movement of the pallet 16 in a forward or rearward direction as desired.

In another exemplary embodiment of a horizontal drive apparatus 212 constructed in accordance with the present invention, the rotary-to-linear motion converting mechanism comprises a threaded lead screw 214 instead of a timing belt. The lead screw 214 extends between and is rotatably supported by a first bearing 216 mounted on the floor plate of the table assembly 14 and positioned adjacent the rear end of the table assembly 14 and a second bearing 218 mounted on the floor plate 32 of the table assembly 14 and positioned adjacent the front end of the table assembly 14. The carriage 24 which supports the pallet 16 is secured to the threaded lead screw 214 through a clamp 220 threadedly received on the lead screw 214 such that rotation of the lead screw 214 causes linear movement of the clamp 220 and the carriage 24. The rotary motor 48 is connected through the floor plate 32 of the table assembly 14 to the lead screw through the gear reducer 50 and the clutch 52.

Figure 8:
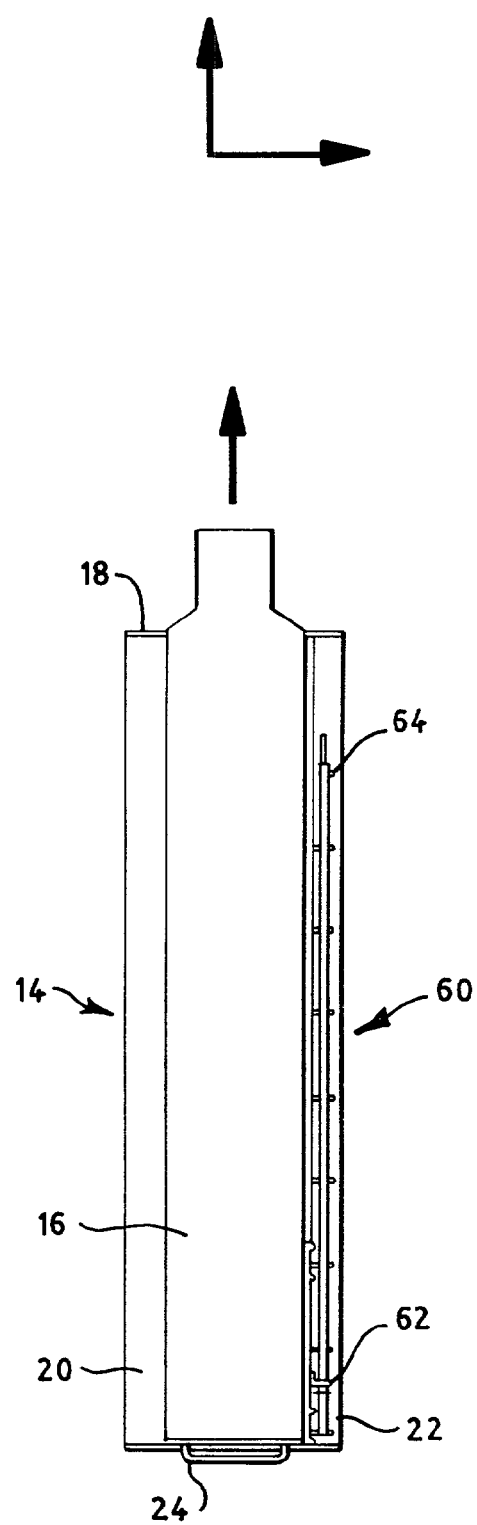
FIGS. 8 and 9 are top plan views of the patient table of FIG. 1, wherein one of the side plates of the table assembly of the table is shown removed to reveal a sensor assembly, showing horizontal movement of the pallet between fully retracted and fully extended positions.
Figure 9:
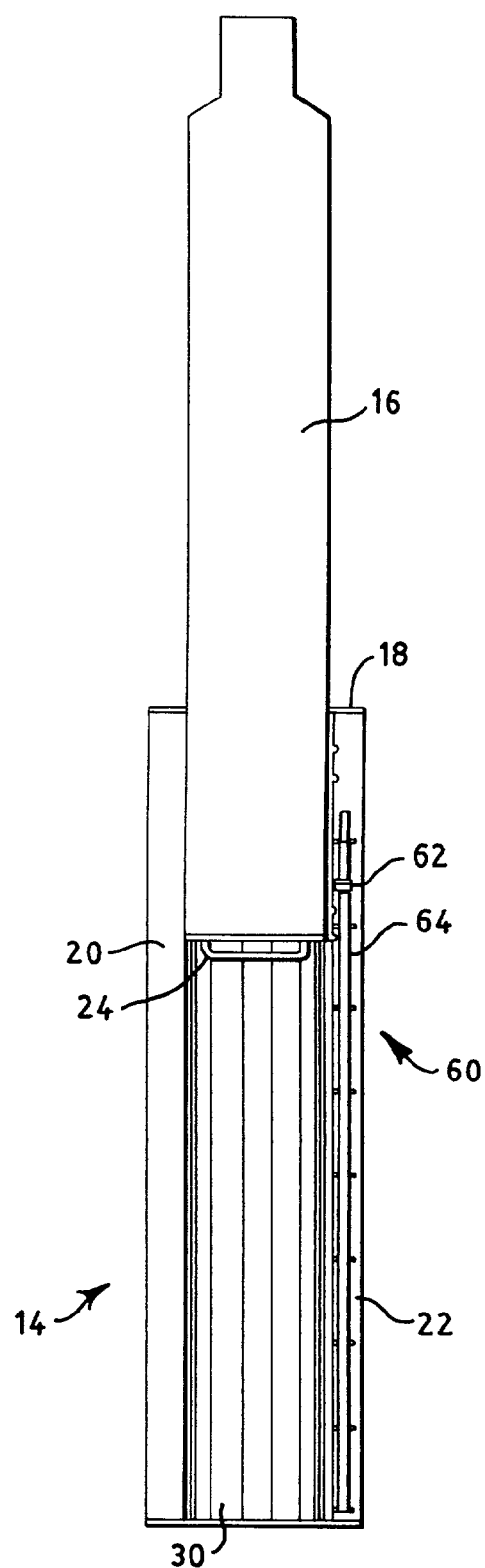

Referring to FIGS. 8 through 10, the patient table 10 is also provided with the new and improved sensor assembly 60 constructed in accordance with the present inventions for providing an indication of an absolute position of the carriage 24 with respect to the table assembly 14. The sensor assembly 60 includes a magnet 62 secured to the carriage 24 of the pallet 16 and a magnetic absolute linear position sensor 64 secured to a flange of one of the rails 22 of the table assembly 14. The relative position of the carriage 24 with respect to the magnetic sensor 64 of the table assembly 14 can then be determined from the output signal provided by the magnetic sensor 64. This horizontal position sensor assembly 60 has been found to provide extremely accurate and consistent horizontal position measurements.

Figure 11:
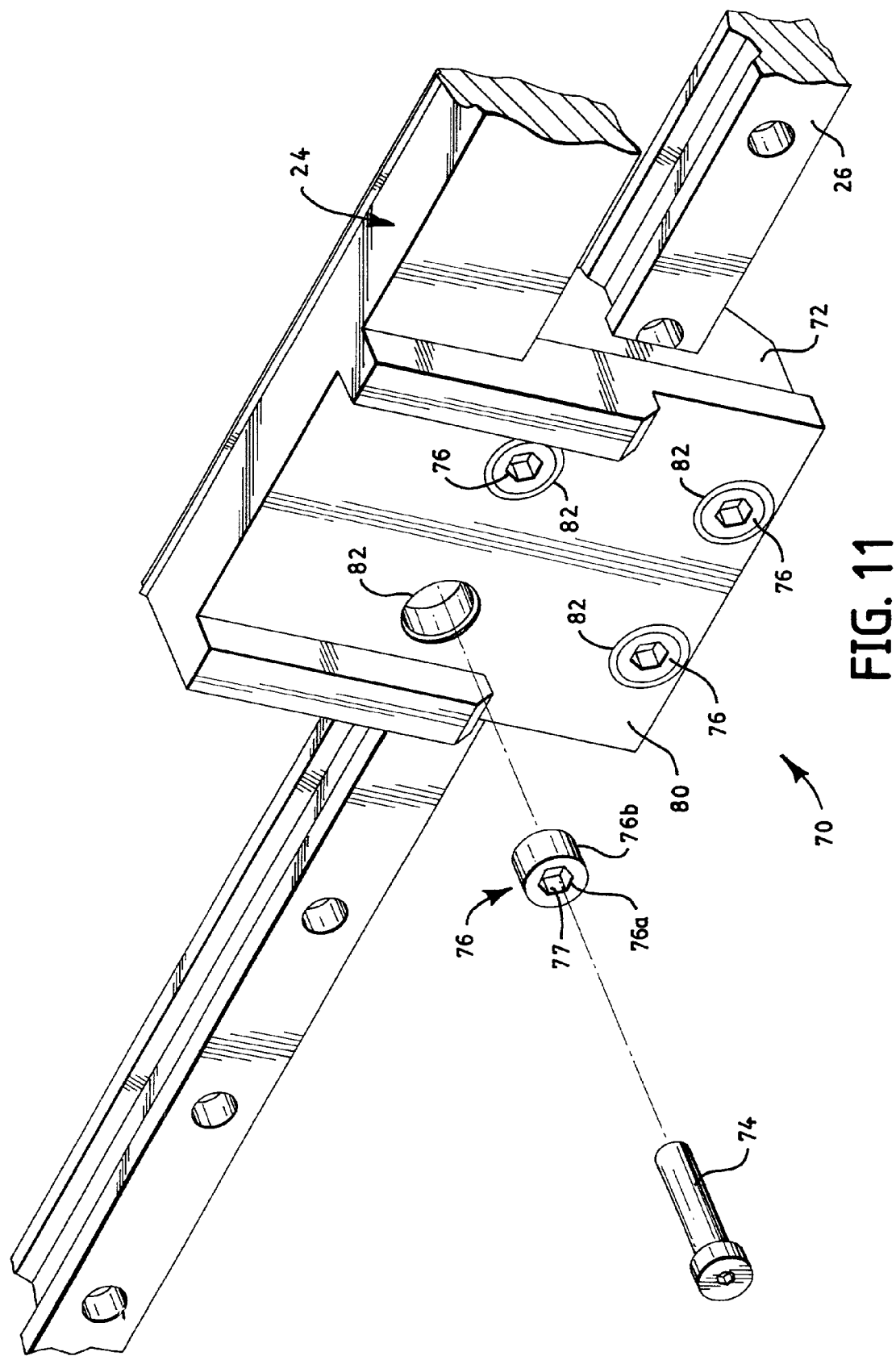
FIG. 11 is an enlarged top and side perspective view of a portion of a track of the table assembly of the table, a portion of the carriage of the pallet, and a bearing supporting the carriage on the track.
Figure 12:
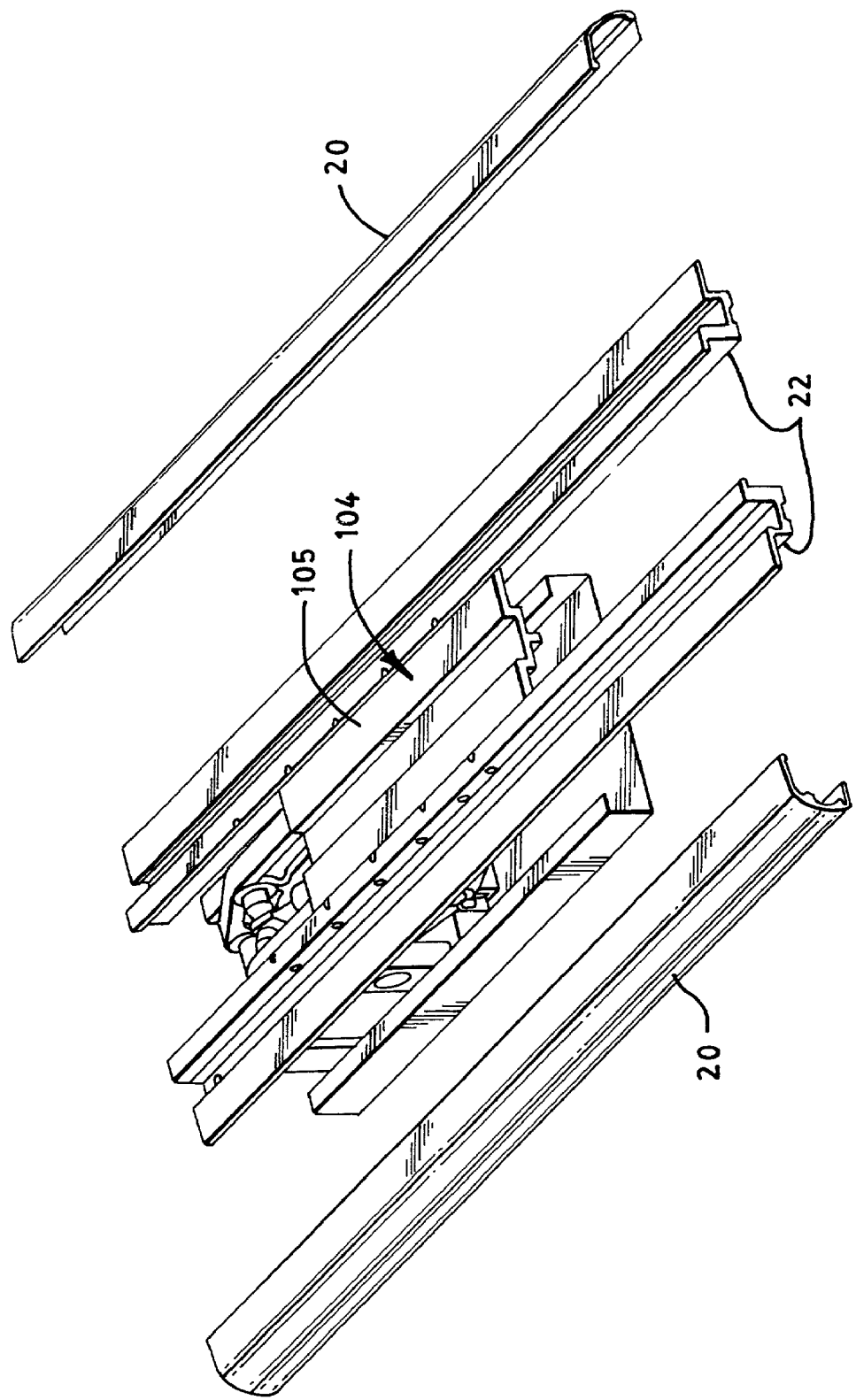
FIG. 12 is a top and end perspective view of the lifting apparatus of the patient table of FIG. 1, and exploded pieces of the table assembly.
Figure 13:
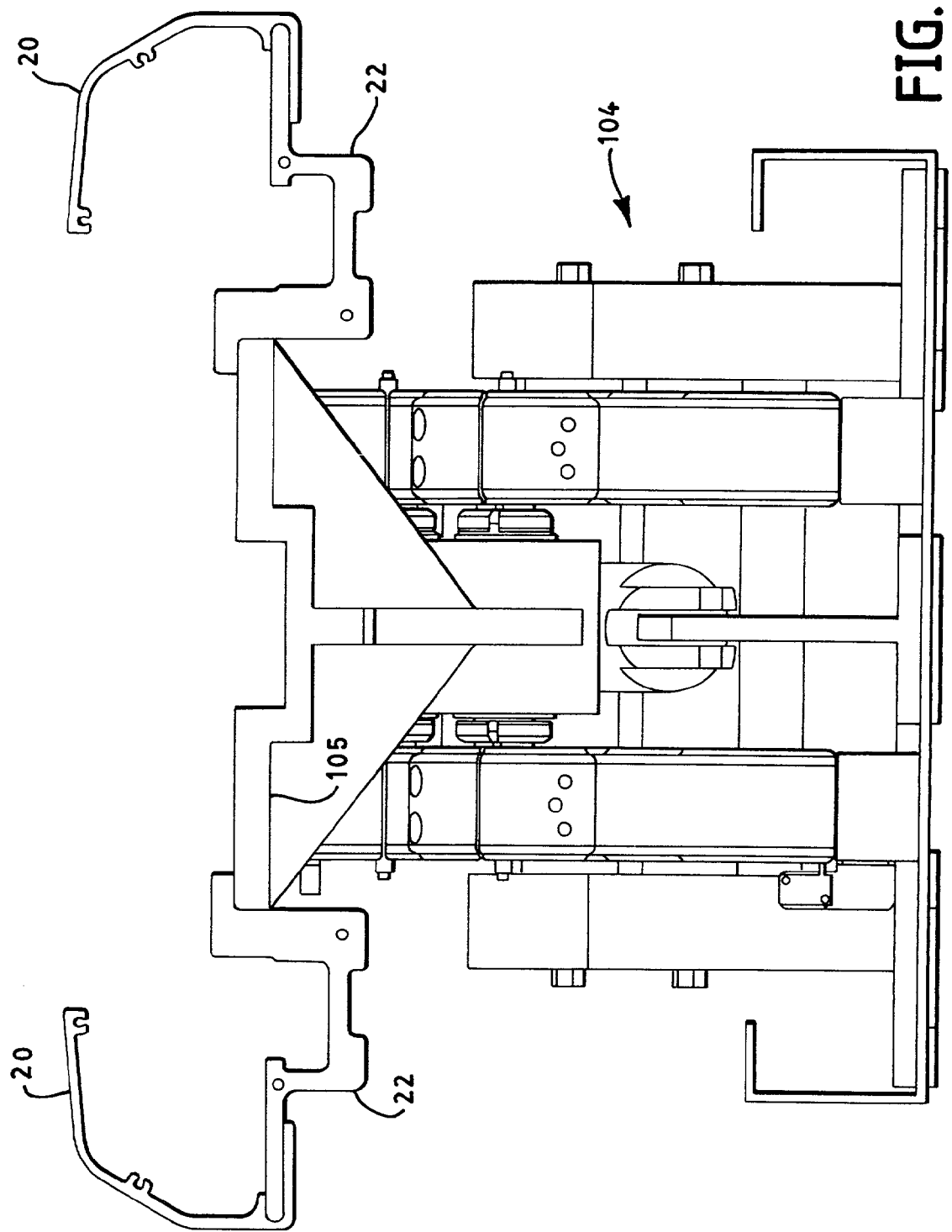
FIG. 13 is an end view of the lifting apparatus of the patient table of FIG. 1, and the pieces of the table assembly shown assembled to the lifting apparatus.

Referring to FIGS. 10 and 11, the patient table 10 is also provided with a new and improved bearing assembly 70 constructed in accordance with the present inventions that slidably supports the carriage 24 on the tracks 26 of the table assembly 14. Supports 80 of the carriage 24 are secured to bearing cassettes 72 which ride on the linear tracks 26 of the table assembly 14. The bearing cassettes 72 are secured to the carriage supports 80 with fasteners 74 adjustably extending through sleeves 76, which are in turn adjustably received in bores 82 of the supports 80. Ends of the fasteners 74 are secured in bores (not shown in the figures) of the bearing cassettes 72 to secure the supports 80 to the bearing cassettes. This fastener and sleeve arrangement allows the supports 80 of the carriage 24 to be easily adjusted with respect to the bearing cassettes 72 so that the carriage 24 can be easily and quickly centered between the linear tracks 26 of the table assembly 14.

In the exemplary embodiment shown, the fasteners of the bearing assembly 70 comprise threaded bolts 74, and the bores 82 of the supports 80, and the bores of the cassettes 72 have internal threads. The sleeves 76 have internal threads engaging the external threads of the bolts 74 and external threads engaging the threaded bores 82 of the supports 80. The ends of the threaded bolts 74 are threadedly received in the threaded bores of the bearing cassettes 72. The sleeves 76 also have an internal tool engaging surface 77 for allowing the sleeves to be rotated and adjusted within the threaded bores 82 of the supports 80 using the tool. In the exemplary embodiment shown, the internal tool engaging surface comprises a hex socket 77 for receiving a hex head driver tool.

While the patient table 10 of the present inventions are described and shown as being used with an x-ray tomography machine, the patient table 10 can also be used in other applications.

It should be understood that the embodiments of the present inventions described herein are merely exemplary and that a person skilled in the art may make variations and modifications to the embodiments described without departing from the spirit and scope of the present inventions. All such equivalent variations and modifications are intended to be included within the scope of these inventions as defined by the appended claims.

What is claimed is:

1. A patient table comprising:
   an elongated table assembly extending between opposing ends;
   an elongated pallet mounted on the table assembly for linear motion between the opposing ends of the table assembly; and
   an elongated horizontal drive apparatus including,
      a rotary motor, and
      an elongated rotary-to-linear motion converting mechanism extending between the opposing ends of the table assembly and substantially positioned at a midpoint between opposing sides of the table assembly, the rotary-to-linear motion converting mechanism connecting the rotary motor to the pallet such that operation of the motor causes linear motion of the pallet on the table assembly, wherein the table assembly is constructed from at least two extruded pieces, and the extruded pieces of the table assembly includes two elongated rails supporting the horizontal drive apparatus, and two elongated external side plates attached to the rails.

2. A patient table according to claim 1, wherein the rotary-to-linear motion converting mechanism comprises:
   a timing pulley connected to the rotary motor and rotatably mounted on the table assembly adjacent a first of the opposing ends of the table assembly;
   an idler pulley rotatably mounted on the table assembly adjacent a second of the opposing ends of the table assembly;
   a continuous timing belt extending between the timing pulley and the idler pulley; and
   a clamp securing the pallet to the timing belt.

3. A patient table according to claim 1, wherein the rotary-to-linear motion converting mechanism comprises:
   an elongated threaded lead screw connected to the rotary motor and rotatably supported by a first bearing mounted adjacent a first of the opposing ends of the table assembly and a second bearing mounted adjacent a second of the opposing ends of the table assembly; and
   a clamp connected to the pallet and threadedly received on the lead screw, such that rotation of the lead screw causes linear movement of the clamp and the pallet along the lead screw.

4. A patient table according to claim 1, wherein the motor is connected to the motion converting mechanism through a clutch.

5. A patient table according to claim 4, wherein the clutch is free floating.

6. A patient table according to claim 1, wherein the motor is connected to the motion converting mechanism through a gear reducer.

7. A patient table according to claim 1, further including a sensor assembly comprising:
   a magnet secured to one of the pallet and the table assembly; and
   a magnetic absolute linear position sensor secured to the other of the pallet and the table assembly.

8. A patient table according to claim 7, wherein the magnet is secured to the pallet and the linear position sensor is secured to the table assembly.

9. A patient table according to claim 1, wherein the side plates are snap-fitted to the rails.

10. A patient table according to claim 1, further including opposing end plates secured to ends of the rails and the side plates.

11. A patient table according to claim 1, further comprising:
tracks mounted on opposing sides of the table assembly and extending between the opposing ends of the table assembly; and
a carriage received on the tracks for movement along the tracks between the opposing ends of the table assembly, wherein the pallet is secured to the carriage.

12. A patient table comprising:
an elongated table assembly extending between opposing ends;
tracks mounted on opposing sides of the table assembly and extending between the opposing ends of the table assembly,
a carriage received on the tracks for movement along the tracks between the opposing ends of the table assembly;
an elongated pallet secured to the carriage for linear motion between the opposing ends of the table assembly;
an elongated horizontal drive apparatus including,
a rotary motor, and
an elongated rotary-to-linear motion converting mechanism extending between the opposing ends of the table assembly and substantially positioned at a midpoint between opposing sides of the table assembly, the rotary-to-linear motion converting mechanism connecting the rotary motor to the carriage such that operation of the motor causes linear motion of the pallet on the table assembly; and
a bearing assembly supporting the carriage on the tracks and including,
at least one cassette slidingly received on each of the tracks;
supports connected to the carriage and positioned adjacent the cassettes;
sleeves adjustably received within bores of the supports; and
fasteners adjustably extending through the sleeves and secured in bores of the cassettes.

13. A patient table according to claim 12, wherein the table assembly is constructed from at least two elongated rails supporting the horizontal drive apparatus, and two elongated external side plates attached to the rails.

14. An x-ray tomography scanner system including the patient table of claim 12, and further comprising an annular gantry rotatable about a horizontal center of rotation and containing therein an x-ray source for projecting a beam of x-rays across the center of rotation to a detector array on an opposite side of the gantry, wherein the horizontal drive apparatus can be used to horizontally extend and retract the pallet with respect to the table assembly such that a patient lying on the pallet can be inserted into the annular gantry parallel with the center of rotation of the gantry.

15. A patient table according to claim 14, wherein the fasteners comprise bolts having outer threaded surfaces, the bores of the cassettes include inner threaded surfaces engaging the outer threaded surfaces of the bolts, the sleeves includes inner threaded surfaces receiving engaging the outer threaded surfaces of the bolts and outer threaded surfaces, and the bores of the carriage supports include inner threaded surfaces engaging the outer threaded surfaces of the sleeves.

16. A patient table according to claim 12, wherein the sleeves include internal tool engaging surfaces.

17. A patient table according to claim 12, further including rollers mounted on the table assembly and supporting the pallet.

18. A patient table comprising:
an elongated table assembly extending between opposing ends;
tracks mounted on opposing sides of the table assembly and extending between the opposing ends of the table assembly;
a carriage received on the tracks for linear motion along the tracks between the opposing ends of the table assembly,
an elongated pallet mounted on the carriage; and
an elongated horizontal drive apparatus substantially positioned at a midpoint between the tracks and including,
an elongated threaded lead screw rotatably supported by a first bearing mounted adjacent a first of the opposing ends of the table assembly and a second bearing mounted adjacent a second of the opposing ends of the table assembly, and
a clamp connected to the carriage and threadedly received on the lead screw, such that rotation of the lead screw causes linear movement of the clamp and the pallet along the lead screw;
a bearing assembly supporting the carriage on the tracks and including,
at least one cassette slidingly received on each of the tracks,
supports connected to the carriage and positioned adjacent the cassettes,
sleeves adjustably received within bores of the supports, and
fasteners adjustably extending through the sleeves and secured in bores of the cassettes.

* * * * *